United States Patent [19]

Schropp

[11] Patent Number: 4,828,652

[45] Date of Patent: May 9, 1989

[54] REMOVAL OF ALDEHYDES FROM α, β-OLEFINICALLY UNSATURATED CARBOXYLIC ACIDS

[75] Inventor: Wilhelm K. Schropp, Weinheim, Fed. Rep. of Germany

[73] Assignee: BASF Aktiengesellschaft, Ludwigshafen, Fed. Rep. of Germany

[21] Appl. No.: 127,048

[22] Filed: Dec. 1, 1987

[30] Foreign Application Priority Data

Dec. 9, 1986 [DE] Fed. Rep. of Germany ....... 3641996

[51] Int. Cl.$^4$ ...................... B01D 3/34; C07C 57/075
[52] U.S. Cl. .......................... 203/38; 203/59; 203/91; 203/DIG. 21; 562/600
[58] Field of Search ...................... 203/38, 6, DIG. 21, 203/59, 8, 58, 57, 91, 33, 34; 562/600, 598, 599; 560/4, 218

[56] References Cited

U.S. PATENT DOCUMENTS

| | | | |
|---|---|---|---|
| 3,725,208 | 4/1973 | Maezawa et al. | 203/DIG. 21 |
| 3,893,895 | 7/1975 | Dehnert et al. | 203/DIG. 21 |
| 3,926,744 | 12/1975 | Noll et al. | 203/DIG. 21 |
| 4,146,735 | 3/1979 | Carpenter et al. | 562/600 |
| 4,358,347 | 11/1982 | Mettetal et al. | 203/DIG. 21 |

FOREIGN PATENT DOCUMENTS

| | | | |
|---|---|---|---|
| 48-31087 | 9/1973 | Japan | 562/600 |
| 49-95920 | 9/1974 | Japan | 562/600 |
| 52-23017 | 2/1977 | Japan | 562/600 |
| 56-18934 | 2/1981 | Japan | 562/600 |
| 57-88143 | 6/1982 | Japan | 562/600 |
| 61-218556 | 9/1986 | Japan | 562/600 |
| 1346737 | 2/1974 | United Kingdom . | |

Primary Examiner—Wilbur Bascomb
Attorney, Agent, or Firm—Oblon, Fisher, Spivak, McClelland & Maier

[57] ABSTRACT

Aldehydes are removed from α,β-olefinically unsaturated monocarboxylic acids of 3 or 4 carbon atoms by adding hydrazine derivatives and distilling the unsaturated monocarboxylic acids if the hydrazine derivatives used are aminoguanidine and/or aminoguanidine salts in amounts of from 1 to 3 moles per mole of aldehyde.

7 Claims, No Drawings

REMOVAL OF ALDEHYDES FROM α,β-OLEFINICALLY UNSATURATED CARBOXYLIC ACIDS

α,β-olefinically unsaturated carboxylic acids of 3 or 4 carbon atoms, in particular acrylic acid and methacrylic acid, which have been prepared by catalytic gas phase oxidation of the corresponding alkenes usually contain from the synthesis small amounts of carbonyl compounds, in particular aldehydes, of which in particular furfural interferes in further processing. Further carbonyl compounds are for example acrolein, propionaldehyde and benzaldehyde. For instance, the technical-grade acrylic acid produced by the gas phase oxidation of propylene frequently contains from 250 to 400 ppm of furfural. If such an α,β-olefinically unsaturated carboxylic acid is esterified in the presence of sulfuric acid, troublesome deposits are formed in the apparatus. In addition, furfural can act as a regulant in the polymerization of such acrylic acid and thus interfere with the production of high molecular weight polymers.

Past attempts have therefore concentrated on drastically reducing the aldehyde content, in particular the furfural content, by addition of hydrazine or aqueous hydrazine solutions and distillation of the α,β-olefinically unsaturated carboxylic acid, but this idea has only succeeded in producing an α,β-olefinically unsaturated carboxylic acid having a furfural content of less then 5 ppm by using an excess of about 4 moles of hydrazine and special distillation conditions, although the distillation column rapidly becomes coated with byproducts, so that the plant needs to be flushed out every few days.

Apart from hydrazine, other compounds already used for removing aldehydes from crude acrylic acid by the process of GB Pat. No. 1,346,737 are phenylhydrazine, aniline, monoethanolamine and ethylenediamine, although the lowest residual aldehyde contents were obtained with hydrazine and phenylhydrazine.

We have now found that aldehydes can be advantageously removed from α,β-olefinically unsaturated carboxylic acids of 3 or 4 carbon atoms by adding hydrazine derivatives and distilling the unsaturated monocarboxylic acid if the hydrazine derivatives used are aminoguanidine and/or aminoguanidine salts in amounts of from 1 to 3 moles per mole of aldehyde. Aminoguanidine and its salts, in particular aminoguanidine hydrogencarbonate, are readily commercially obtainable. They are substantially less toxic than hydrazine and can be used in a purity of about 99%. Unlike hydrazine, therefore, no additional water is brought in. In the novel process, the aminoguanidine and/or an aminoguanidine salt, such as the hydrogencarbonate, nitrate, sulfate or chloride, of which preference is given to aminoguanidine hydrogencarbonate, is used in an amount of from 1 to 3 moles per mole of aldehyde. In most cases, amounts of from 1.1 to 2 moles per mole of aldehyde are sufficient. The reaction between aminoguanidine or a salt thereof and acrylic acid is significantly slower than a corresponding reaction of hydrazine with acrylic acid, and the products formed by aminoguanidine salts thereof with the aldehyde contaminants do not tend to split up again or react further in the course of the distillative removal of the pure α,β-olefinically unsaturated monocarboxylic acid. Finally, aminoguanidine and its salts safely combine with all the aldehydes present as contaminants, and there is no secondary reaction to give troublesome benzaldehyde.

In the industrial practice of the novel process, the aminoguanidine and/or the aminoguanidine salts are usually added to the α,β-olefinically unsaturated monocarboxylic acid in amounts of from 1 to 2 moles per mole of aldehyde, preferably in an amount from 1.1 to 1.5 moles per mole of aldehyde. For further purification, the α,β-olefinically unsaturated monocarboxylic acid is then distilled, in general under a reduced pressure of from 10 to 100 mbar. The distillation can be carried out as early as a short time after addition of aminoguanidine and/or salts thereof, or alternatively, hours or days later and in the additional presence of polymerization inhibitors such as hydroquinone or hydroquinone monomethyl ether in customary amounts.

EXAMPLE 1

To technical-grade acrylic acid produced by catalytic gas phase oxidation of propylene in a conventional manner and containing 380 ppm of furfural (F) and 30 ppm of benzaldehyde (B) are added, at room temperature, 1.5 or 2.5 mol of aminoguanidine hydrocarbonate (AGHC) per mol of aldehyde. The mixtures are analyzed at intervals for aldehyde by gas chromatography. The following result is obtained:

TABLE 1

| Duration | 1.5 mol of AGHC | | 2.5 mol of AGHC | |
|---|---|---|---|---|
| | ppm of F | ppm of B | ppm of F | ppm of B |
| 0 | 380 | 30 | 380 | 30 |
| 0.5 hour | 15 | 3 | <1 | <1 |
| 1.5 hours | <1 | <1 | <1 | <1 |
| 4 hours | <1 | <1 | <1 | <1 |
| 1 day | <1 | <1 | <1 | <1 |
| 5 days | <1 | <1 | <1 | <1 |

Distillation of the mixtures under a reduced pressure of 50 mbar after 4 hours gives the same distillation product as after 5 days, namely an acrylic acid containing less than 1 ppm of aldehyde. Moreover, distillation is found to be trouble-free.

COMPARATIVE TEST 1

Technical-grade acrylic acid of the type specified in Example 1 is treated with 1.5 or 2.5 mol/mol of aldehyde, the hydrazine being used in the form of a 25% strength aqueous hydrazine hydrate solution. Analysis by gas chromatography revealed the following residual aldehyde contents:

TABLE 2

| Duration | 1.5 mol of hydrazine | | 2.5 mol of hydrazine | |
|---|---|---|---|---|
| | ppm of F | ppm of B | ppm of F | ppm of B |
| 0 | 380 | 30 | 380 | 30 |
| 0.5 hour | 1 | 1 | 1 | 1 |
| 2 hours | 2 | <1 | <1 | <1 |
| 5 hours | 10 | 1 | 3 | <1 |
| 1 day | 52 | 19 | 1 | 62 |
| 5 days | 40 | 111 | <1 | 178 |

Only if the mixture is immediately distilled under reduced pressure (50 mbar) after the hydrazine has been added is it possible to obtain a virtually aldehydefree acrylic acid, although it does not take long for the distillation apparatus to become coated with polymeric products insoluble in acrylic acid and these are not avoidable even by increasing the dosage of stabilizers customary in distillation, such as phenothiazine.

If the mixture of acrylic acid with hydrazine hydrate is distilled more than 2 hours after hydrazine is added, the distillation products obtained again contain aldehydes, in the case of benzaldehyde in an amount which can be greater than the original amount.

EXAMPLE 2

To a methacrylic acid produced by gas phase oxidation from methacrolein (M) and containing 20 ppm of methacrolein, 20 ppm of furfural and 15 ppm of benzaldehyde are added 2.5 mol of aminoguanidine hydrogencarbonate. Shortly after the AGHC has been added, gas chromatography of the mixture shows that aldehyde is no longer present (detection limit 1 ppm). If the mixture is distilled under reduced pressure (50 mbar) after 3 hours or after 3 days, the result obtained is a methacrylic acid in which no aldehyde is detectable by gas chromatography.

COMPARATIVE TEST 2

To a methacrylic acid of the composition specified in Example 2 are added 2.5 mol of hydrazine in the form of a 25% strength aqueous hydrazine hydrate solution. The mixture is analyzed for aldehyde by gas chromatography. The following results are obtained:

TABLE 3

| Duration | ppm of M | ppm of F | ppm of B |
|---|---|---|---|
| 0 | 20 | 20 | 15 |
| 1.5 hours | 6 | 4 | 2 |
| 3 hours | <1 | 2 | <1 |
| 4 hours | <1 | 1 | <1 |
| 1 day | <1 | 3 | 5 |
| 5 days | <1 | 7 | 11 |

If the mixture of methacrylic acid and hydrazine hydrate solution is distilled, a virtually aldehyde-free methacrylic acid is only obtained if the reduced pressure distillation is carried out about 4 hours after the components were mixed. If, however, the mixture is left to stand for a prolonged period, it is found that in the reduced pressure distillation the furfural and benzaldehyde contents in the methacrylic acid distillate are again on the increase.

I claim:

1. A process for removing aldehydes from an $\alpha,\beta$-olefinically unsaturated monocarboxylic acid of 3 or 4 carbon atoms comprising adding aminoguanidine, or aminoguanidine salts or a mixture thereof in amounts of from 1 to 3 moles per mole of aldehyde, and distilling the unsaturated monocarboxylic acid.

2. A process as claimed in claim 1, wherein the aminoguanidine salt is aminoguanidine hydrogencarbonate.

3. The process according to claim 1, wherein said aminoguanidine, aminoguanidine salts or a mixture there of is added in the amount of from about 1 to 2 moles per mole of aldehyde.

4. The process according to claim 3, wherein said aminoguanidine, aminoguanidine salts or a mixture thereof is added in the amount of about 1.1 to 1.5 moles per mole of aldehyde.

5. The process according to claim 1, wherein said $\alpha,\beta$-olefinically unsaturated monocarboxylic acid is distilled under a reduced pressure of from 10 to 100 mbar.

6. The process according to claim 1, wherein said distillation is effected after at least about one and one-half hours after adding said aminoguanidine, aminoguanidine salts or a mixture thereof to said $\alpha,\beta$-olefinically unsaturated monocarboxylic acid.

7. The process according to claim 1, wherein after distillation less than 1 ppm of aldehyde is present in said $\alpha,\beta$-olefinically unsaturated monocarboxylic acid.

* * * * *